(12) United States Patent
McDonald et al.

(10) Patent No.: US 9,833,610 B2
(45) Date of Patent: Dec. 5, 2017

(54) SYSTEMS AND METHODS FOR MAKING AND USING ELECTRODE OR TERMINAL EXTENSIONS FOR COUPLING TO LEADS OF IMPLANTABLE ELECTRICAL SYSTEMS

(71) Applicant: Boston Scientific Neuromodulation Corporation, Valencia, CA (US)

(72) Inventors: Matthew Lee McDonald, Pasadena, CA (US); Jacob Matthew Muhleman, Canandaiuga, NY (US); Rafael Carbunaru, Valley Village, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 15/064,321

(22) Filed: Mar. 8, 2016

(65) Prior Publication Data
US 2016/0184577 A1 Jun. 30, 2016

Related U.S. Application Data

(62) Division of application No. 13/864,906, filed on Apr. 17, 2013, now Pat. No. 9,308,364.

(51) Int. Cl.
*A61N 1/00* (2006.01)
*A61N 1/05* (2006.01)
(Continued)

(52) U.S. Cl.
CPC .............. *A61N 1/05* (2013.01); *A61N 1/0551* (2013.01); *H01R 24/58* (2013.01); *H01R 31/02* (2013.01);
(Continued)

(58) Field of Classification Search
None
See application file for complete search history.

(56) References Cited

U.S. PATENT DOCUMENTS

| 6,181,969 B1 | 1/2001 | Gord |
| 6,516,227 B1 | 2/2003 | Meadows et al. |
| (Continued) | | |

OTHER PUBLICATIONS

Official Communication for U.S. Appl. No. 13/864,906 dated Jul. 30, 2015.

*Primary Examiner* — Christopher D Koharski
*Assistant Examiner* — Elizabeth K So
(74) *Attorney, Agent, or Firm* — Lowe Graham Jones PLLC; Bruce E. Black

(57) ABSTRACT

A lead assembly includes an implantable lead. Electrodes are disposed along a distal end of the lead in an electrode array. Terminals are disposed along a proximal end of the lead in a proximal-most terminal array and a medial terminal array. A terminal extension electrically couples to the medial terminal array. A port is defined in a connector at a first end of the terminal extension. The port has a first end and an opposing second end and forms a continuous passageway therebetween. The port receives the medial terminal array. A contact array includes connector contacts that are disposed within the port and that couple electrically with a terminal array disposed along a second end of the terminal extension. The contact array couples electrically with terminals of the medial terminal array of the lead when the medial terminal array is received by the port.

20 Claims, 7 Drawing Sheets

(51) Int. Cl.
*H01R 24/58* (2011.01)
*H01R 31/02* (2006.01)
*A61N 1/04* (2006.01)

(52) U.S. Cl.
CPC .......... *A61N 1/0472* (2013.01); *A61N 1/0476* (2013.01); *H01R 2201/12* (2013.01)

(56) References Cited

U.S. PATENT DOCUMENTS

| | | |
|---|---|---|
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,672,734 B2 | 3/2010 | Anderson et al. |
| 7,761,165 B1 | 7/2010 | He et al. |
| 7,949,395 B2 | 5/2011 | Kuzma |
| 7,974,706 B2 | 7/2011 | Moffitt et al. |
| 8,175,710 B2 | 5/2012 | He |
| 8,364,278 B2 | 1/2013 | Pianca et al. |
| 2007/0150036 A1 | 6/2007 | Anderson |
| 2011/0029052 A1* | 2/2011 | McDonald ........... A61N 1/0551 607/116 |
| 2011/0034978 A1 | 2/2011 | McDonald |

* cited by examiner

SYSTEMS AND METHODS FOR MAKING AND USING ELECTRODE OR TERMINAL EXTENSIONS FOR COUPLING TO LEADS OF IMPLANTABLE ELECTRICAL SYSTEMS

CROSS-REFERENCE TO RELATED APPLICATIONS

This application is a divisional of U.S. patent application Ser. No. 13/864,906 (now U.S. Pat. No. 9,308,364) filed on Apr. 17, 2013 which claims the benefit under 35 U.S.C. §119(e) of U.S. Provisional Patent Application Ser. No. 61/635,175 filed on Apr. 18, 2012, both of which are incorporated herein by reference.

FIELD OF THE INVENTION

The present invention is directed to the area of implantable electrical stimulation systems and methods of making and using the systems. The present invention is also directed to implantable electrical stimulation systems having electrode extensions for coupling to electrodes of leads or terminal extensions for coupling to terminals of leads or both, as well as methods of making and using the electrode extensions, terminal extensions, and leads.

BACKGROUND

Implantable electrical stimulation systems have proven therapeutic in a variety of diseases and disorders. For example, spinal cord stimulation systems may be implanted in the spinal cord to treat chronic pain syndromes and in the brain to treat refractory chronic pain syndromes, movement disorders, and epilepsy. Peripheral nerve stimulation systems may be used to treat chronic pain syndrome and incontinence. In some cases, paralyzed extremities in spinal cord injury patients may be treated using functional electrical stimulation. Moreover, electrical stimulation systems can be implanted subcutaneously to stimulate subcutaneous tissue including subcutaneous nerves such as the occipital nerve.

In general, a stimulator includes a control module (with a pulse generator), one or more leads, and an array of stimulator electrodes mounted on the one or more leads. The stimulator electrodes are placed in contact with (or near) the nerves, muscles, or other tissue to be stimulated. The pulse generator in the control module generates electrical pulses that are delivered through the electrodes to body tissue.

BRIEF SUMMARY

In one embodiment, a lead assembly for an implantable electrical stimulation system includes a lead configured and arranged for insertion into a patient. The lead includes a lead body having a distal end, a proximal end, and a longitudinal length. A plurality of electrodes are disposed along the distal end of the lead body and are arranged into at least one electrode array. A plurality of terminals are disposed along the proximal end of the lead body and are arranged into a plurality of terminal arrays, where each terminal array includes a plurality of the terminals. The plurality of terminal arrays includes a proximal-most terminal array and a medial terminal array axially-spaced-apart from one another along the longitudinal length of the lead body with the medial terminal array being disposed distal to the proximal-most terminal array along the longitudinal length of the lead body. A plurality of conductors electrically couples the plurality of electrodes to at least one of the plurality of terminals. A terminal extension is configured and arranged to electrically couple to the medial terminal array. The terminal extension includes a terminal extension body having a first end and an opposing second end. A terminal extension connector is disposed at the first end of the terminal extension body. A port is defined in the terminal extension connector. The port has a first end and an opposing second end and forms a continuous passageway therebetween. The port is configured and arranged to receive the medial terminal array. A connector contact array includes a plurality of connector contacts disposed within the port. The connector contact array is configured and arranged to couple electrically with terminals of the medial terminal array when the medial terminal array is received by the port. A terminal extension terminal array includes a plurality of terminals disposed along the second end of the terminal extension body. A plurality of terminal extension conductors electrically couples the connector contact array to the terminal extension terminal array.

In another embodiment, a lead assembly for an implantable electrical stimulation system includes a lead configured and arranged for insertion into a patient. The lead includes a lead body having a distal end, a proximal end, and a longitudinal length. A plurality of electrodes are disposed along the proximal end of the lead body and are arranged into a plurality of electrode arrays, where each electrode array includes a plurality of the electrodes. The plurality of electrode arrays includes a distal-most electrode array and a medial electrode array axially-spaced-apart from one another along the longitudinal length of the lead body with the medial electrode array being disposed proximal to the distal-most electrode array along the longitudinal length of the lead body. A plurality of terminals are disposed along the distal end of the lead body and are arranged into at least one terminal array. A plurality of conductors electrically couple the plurality of electrodes to at least one of the plurality of terminals. An electrode extension is configured and arranged to electrically couple to the medial electrode array. The electrode extension includes an electrode extension body having a first end and an opposing second end. An electrode extension connector is disposed at the first end of the electrode extension body. A port is defined in the electrode extension connector. The port has a first end and an opposing second end and forms a continuous passageway therebetween. The port is configured and arranged to receive the medial electrode array. A connector contact array includes a plurality of connector contacts disposed within the port. The connector contact array is configured and arranged to couple electrically with terminals of the medial electrode array when the medial electrode array is received by the port. An electrode extension electrode array includes a plurality of electrodes disposed along the second end of the electrode extension body. A plurality of electrode extension conductors electrically couples the connector contact array to the electrode extension electrode array.

In yet another embodiment, a lead assembly for an implantable electrical stimulation system includes a lead configured and arranged for insertion into a patient. The lead includes a lead body having a distal end, a proximal end, and a longitudinal length. A plurality of electrodes are disposed along the lead body and arranged into at least one distal electrode array disposed along the distal end of the lead body and at least one proximal electrode array disposed along the proximal end of the lead body. A plurality of terminals are disposed along the lead body and arranged into a plurality of terminal arrays, where each terminal array includes a plurality of the terminals. The plurality of terminal arrays includes a first medial terminal array and a second medial terminal array axially-spaced-apart from one another along the longitudinal length of the lead body. The first medial terminal array and the second medial terminal array are both distal to the proximal-most electrode array and proximal to the distal-most electrode array along the longitudinal length of the lead body. A plurality of conductors electrically couples the plurality of electrodes to at least one of the plurality of terminals.

BRIEF DESCRIPTION OF THE DRAWINGS

Non-limiting and non-exhaustive embodiments of the present disclosure are described with reference to the following drawings. In the drawings, like reference numerals refer to like parts throughout the various figures unless otherwise specified.

For a better understanding of the present disclosure, reference will be made to the following detailed description, which is to be ready in association with the accompanying drawings, wherein.

DETAILED DESCRIPTION

The present invention is directed to the area of implantable electrical stimulation systems and methods of making and using the systems. The present invention is also directed to implantable electrical stimulation systems having electrode extensions for coupling to electrodes of leads or terminal extensions for coupling to terminals of leads or both, as well as methods of making and using the electrode extensions, terminal extensions, and leads.

Embodiments of the present disclosure relate to electrical stimulation systems and related methods of use. Suitable implantable electrical stimulation systems include, but are not limited to, an electrode lead ("lead") with a plurality of electrodes and a plurality of terminals disposed on the lead. The leads include one or more conductors that extend along a length of the lead and electrically couple at least one of the electrodes to at least one of the terminals. Leads include, for example, percutaneous leads, paddle leads, and cuff leads. Examples of electrical stimulation systems with leads are present in, for example, U.S. Pat. Nos. 6,181,969; 6,516,227; 6,609,029; 6,609,032; 6,741,892; 7,244,150; 7,672,734; 7,761,165; 7,949,395; 7,974,706; 8,175,710; and 8,364,278; and U.S. Patent Application Publication No. 2007/0150036, all of which are incorporated by reference.

Figure 1A:
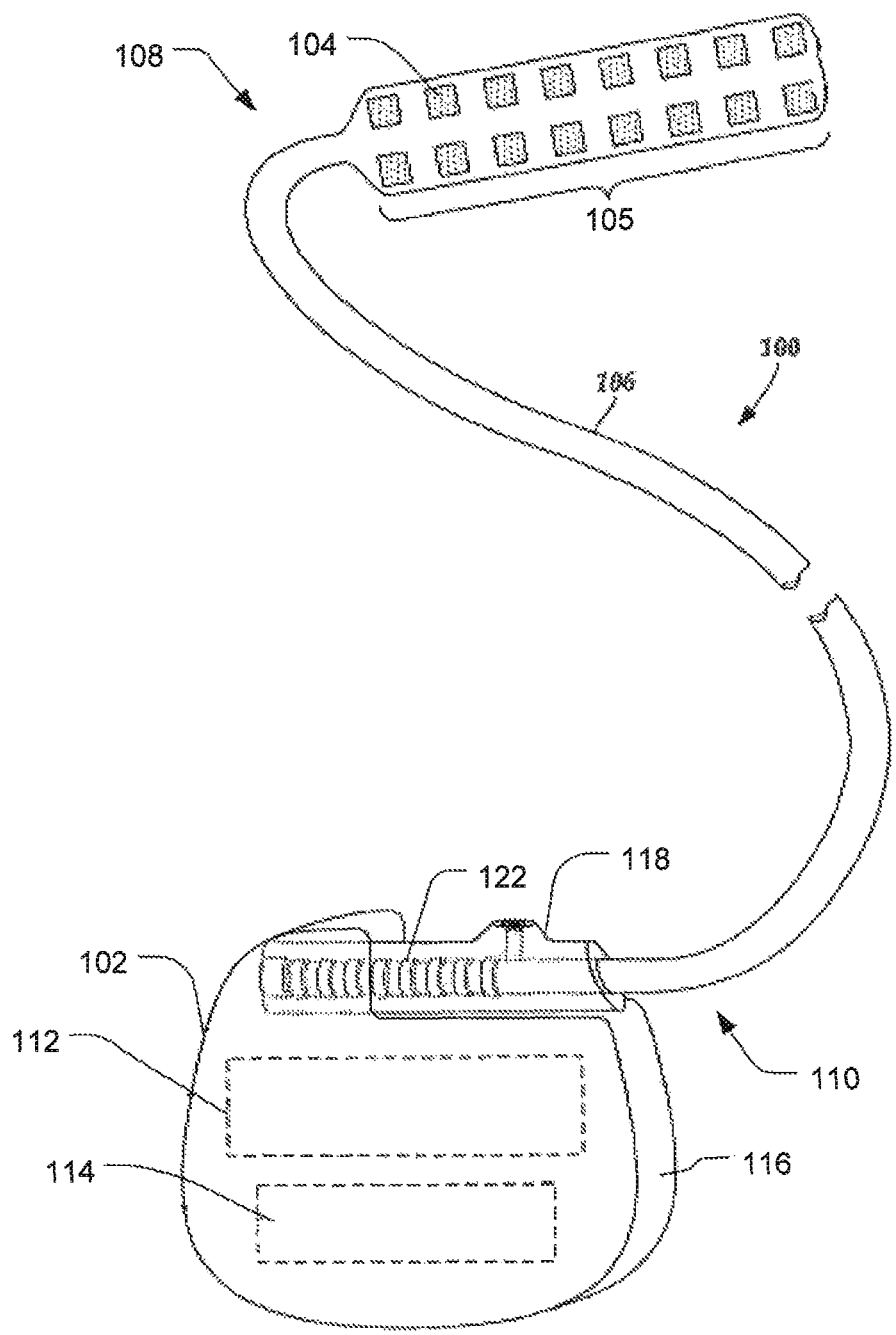
FIG. 1A is a schematic perspective view of one embodiment of a stimulation system, the stimulation system including a control module and a paddle lead inserted into the control module, according to the invention.
Figure 1B:
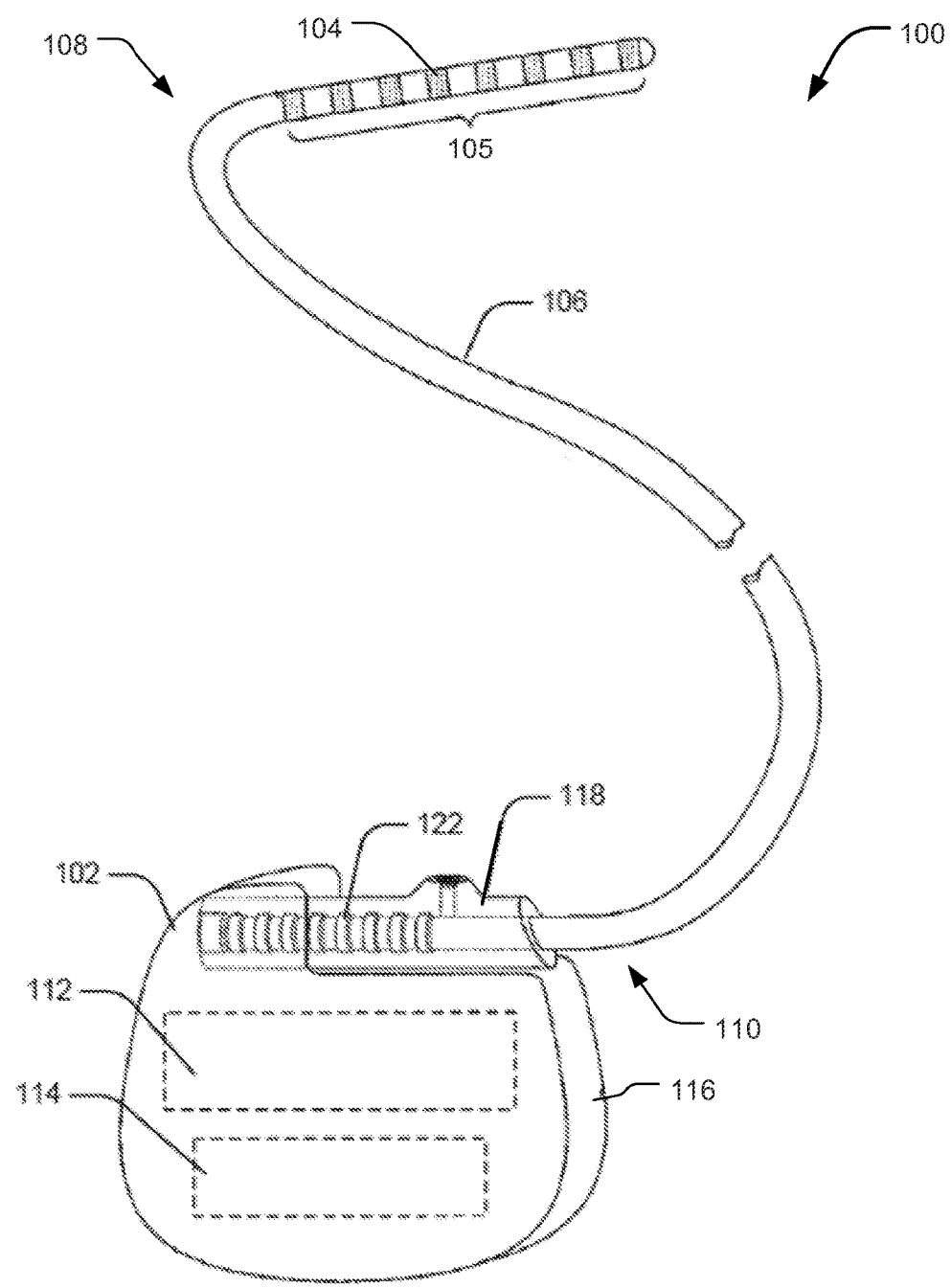
FIG. 1B is a schematic perspective view of another embodiment of the stimulation system of FIG. 1A, the stimulation system including a percutaneous lead inserted into the control module of FIG. 1A, according to the invention.

FIGS. 1A and 1B illustrate two exemplary embodiments of an electrical stimulation system 100 adapted to perform a desired procedure. The electrical stimulation system 100 includes a control module 102, such as a stimulator or pulse generator, and a plurality of electrodes, such as electrode 104, arranged into an array 105. In at least some embodiments, the stimulation system employs a paddle lead, as shown in FIG. 1A, or a percutaneous lead, as shown in FIG. 1B. In at least some embodiments, when the lead 102 is a paddle lead, the electrodes 104 of the array 105 are disposed on a flat, paddle-like surface that is attached to a distal end 108 of the lead 106. A paddle lead can typically stimulate a broader region of patient tissue than a percutaneous lead. In at least some embodiments, when the lead is a percutaneous lead, the electrodes 104 of the array 105 are circumferentially positioned along the distal end 108 of the elongated lead 106. A percutaneous lead can typically be implanted more easily and less invasively than a paddle lead.

One or more components of the stimulation system 100 are typically implanted into the body of a patient for a variety of applications including, for example, brain stimulation, neural stimulation, spinal cord stimulation, or muscle stimulation. A portion of the lead 106, for example, may be implanted in the patient's body with the electrodes 104 at or adjacent a target region and the control module 102 may be disposed external to the patient's body (e.g., strapped to the patient's arm or wrist, taped around the patient's chest, or the like). Alternatively, the entire stimulation system 100 may be implanted in the patient's body. For example, the electrodes 104 may be implanted at a target stimulation region and the control module 102 may be implanted in any suitable area within the body large enough to accommodate the control module 102, such as the abdominal cavity.

The control module 102 typically includes an electronic subassembly 112 and an optional power source 114 disposed in a sealed housing 116. The control module 102 also includes a system connector 118 into which a proximal end 110 of the lead 106 can be plugged to make an electrical connection, via conductive contacts 122 that are disposed in the system connector 118 and that are electrically coupled to the electronic subassembly 112.

The electronic subassembly 112 generates electrical impulses, which are provided to the electrodes 104 through the lead 106. These electrical impulses disrupt pain signals transmitted to the brain from the target nerve, muscle, or organ, thereby reducing or eliminating pain sensed by the patient. Depending on the degree of pain and the location of the target stimulation region, physicians or operators may regulate or modify the strength, duration, and period between impulses using a remote control (not shown). The remote control may be external to the patient's body, and may communicate with the control module 102 through wireless means.

The electrodes 104 can be formed using any suitable conductive, biocompatible material. Examples of suitable material include metals, alloys, conductive polymers, and conductive carbon. The number of electrodes in the electrode array may vary depending on the target area, and the condition being treated. For example, there may be two, four, six, eight, ten, twelve, fourteen, sixteen, or more electrodes. As will be recognized, other numbers of electrodes may also be contemplated.

The electrodes 104 conduct electrical current pulses to stimulate nerve fibers, muscle fibers, or other body tissues. In at least some embodiments, the stimulation system 100 includes a processor that controls the activation, timing, and electrical characteristics of the electrical current pulses. For example, the processor can, if desired, control one or more of the timing, frequency, strength, duration, and waveform of the pulses. In addition, the processor can selectively activate the electrodes 104 for stimulation. In at least some embodiments, the processor is disposed in the control module 102.

Figure 2:
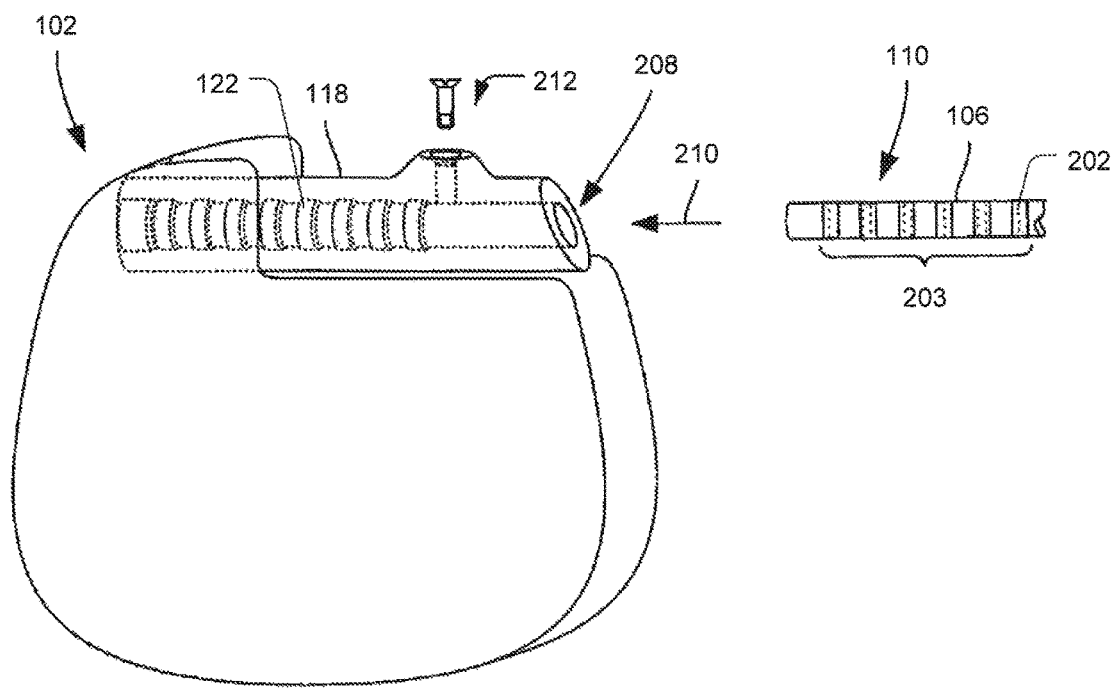
FIG. 2 is a schematic view of one embodiment of a proximal portion of the lead of FIG. 1A or 1B configured for insertion into a connector of the control module of FIG. 1A or 1B, according to the invention.

FIG. 2 illustrates the proximal end 110 of the lead 106 configured for insertion into the system connector 118 of the control module 102. A plurality of terminals, such as terminal 202, are arranged into an array 203 and disposed at the proximal end 110 of the lead 106. The terminal array 203 is configured for connecting electrically to corresponding connector contacts 122, disposed in the connector 118 of the control module 102, upon insertion of the lead 106 into the system connector 118. In at least some embodiments, the number of electrodes 104 is equal to the number of terminals 202. In other embodiments, the number of electrodes 104 is not equal to the number of terminals 202.

Conductive wires ("conductors") (not shown) extend along the lead 106 from the terminals 202 to the electrodes 104. Typically, one or more electrodes 104 of the electrode array 105 are each electrically coupled to different terminals 202 of the array 203. In at least some embodiments, each terminal 202 is connected to a single different electrode 104. The conductors may be embedded in the non-conductive material of the lead 106, or the conductors may be disposed in one or more lumens (not shown) extending along a length of the lead 106. In some embodiments, there is an individual conductor disposed in a single given lumen. In other embodiments, two or more conductors extend through a single given lumen.

The system connector 118 defines at least one port 208 into which the proximal end of lead 106 with terminals 202 may be inserted, as shown by directional arrow 210. FIG. 2 shows the system connector 118 defining a single port. It will be understood that in at least some embodiments the system connector 118 includes a plurality of ports for receiving a plurality of leads (or lead extensions), or a plurality of proximal ends of the body of a single lead.

Each port 208 includes a plurality of connector contacts 122 disposed therein. When the lead 106 is inserted into the port 208, the connector contacts 122 align with the terminals 202 to electrically couple the control module 102 to the electrodes 104. To this end, the terminals 202 and the connector contacts 122 are designed so that each terminal 202 of the terminal array 203 aligns with a corresponding contact 122 of the system connector 118.

Optionally, the lead 106 and the system connector 118 may include corresponding retaining features to fasten the lead 106 to the system connector 118, once the lead 106 is operationally inserted into the port 208. The lead 106 may include a reinforced surface region (309 in FIG. 3A) to which one or more fasteners (e.g., one or more set screws, pins, or the like) 212 may fasten against via a fastener aperture, such as a threaded aperture. Any suitable number of corresponding retaining features can be implemented. In at least some embodiments, a single set of corresponding retaining features are used. In at least some embodiments where the system connector 118 includes a plurality of ports, the number of sets of corresponding retaining features is equal to the number of ports.

Optionally, an elongated lead extension may be used to extend the distance between the control module 102 and the electrodes 104. In which case, the proximal end 110 of the lead 106 may be coupled to lead extension connector contacts disposed in a system connector positioned at a first end of the lead extension, while an opposing second end of the lead extension includes a lead extension terminal array that is electrically coupled to the lead extension connector contacts and that may be received by a system connector of the control module 102 in a manner similar to what is shown in FIGS. 1A-2.

Figure 7:
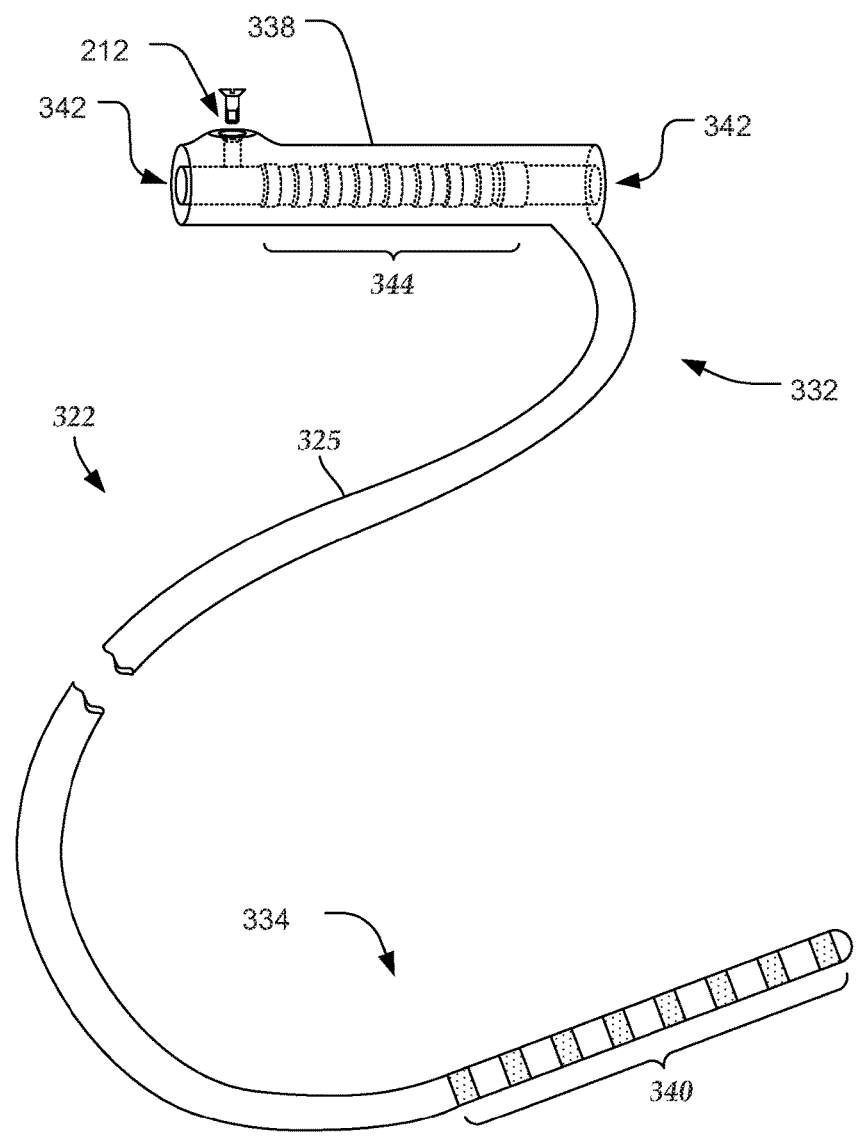
FIG. 7 is a schematic perspective view of one embodiment of a terminal extension suitable for coupling with a terminal array of a lead, according to the invention.

Turning to FIG. 7, in some cases it may be desirable to stimulate a region of patient tissue that is larger than can be effectively stimulated with a lead having a conventional number of electrodes. In which case, it may be useful to form a lead with additional electrodes, as compared to the number of electrodes disposed on conventional stimulation systems. As a result, the number of terminals in the terminal array may, likewise, be increased. The increased number of terminals in the terminal array, however, may prevent the proximal end of the lead from being able to couple directly to the system connector of the control module (or the lead extension). For example, the system connector may be configured to receive two 8-terminal terminal arrays, while the lead has a single 16-terminal terminal array.

One technique for coupling the lead to the system connector when the terminal configuration of the terminal array is different from the connector contact configuration of the system connector is to form the body of the lead with two or more proximal ends, where each of the different proximal ends includes a terminal array adapted for concurrently coupling to the system connector, and where each of the terminal arrays includes terminals coupled to a different sub-set of the electrodes of the lead. For example, when the system connector is configured to receive two 8-terminal terminal arrays, the lead body can be formed with two proximal ends, where each proximal end includes an 8-terminal terminal array coupled to a different sub-set of the electrodes of the lead. Unfortunately, in the case of percutaneous leads, forming two proximal ends of the lead body prevents the lead from being isodiametric and may make implantation of the lead more invasive, as a larger-sized introducer needle may be needed.

Alternately (or additionally), if the terminal configuration of the terminal array is different from the connector contact configuration of the system connector it may be necessary to insert the proximal end of the lead into a splitter or an adaptor to divide up the terminals of a single array into multiple arrays. For example, when the system connector is configured to receive two 8-terminal terminal arrays, and the lead includes a single 16-terminal terminal array, the splitter or adapter may be configured to receive the 16-terminal terminal array and electrically couple each of the terminals to one of two 8-terminal terminal arrays of the splitter or adapter that are compatible with the system connector.

Unfortunately, additional components, such as splitters, adapters, or the like, may increase the size and complexity of the stimulation system, making the system bulkier, fragile, and more prone to error. For example, in the case of a lead with a 16-terminal terminal array, the splitter or adapter may include sixteen connector contacts and two 8-terminal terminal arrays. Additionally the splitter or adapter may need to have two proximal ends and enough conductors to couple each of the sixteen connector contacts to each of the two 8-terminal terminal arrays.

As herein described, a lead assembly may include a lead and a terminal extension coupleable to a terminal array of the lead. The terminal extension may include a connector at a first end and a terminal extension terminal array at an opposing second end. In at least some embodiments, the connector of the terminal extension is coupleable with a lead terminal array and the terminal extension terminal array is coupleable to a system connector of the control module (or a lead extension).

FIG. 7 is a schematic perspective view of one embodiment of a terminal extension 322. suitable for coupling with a terminal array of a lead. The terminal extension 322 includes a body 325 having a first end 332 and an opposing second end 334. A connector 338 is disposed at the first end 332 of the terminal extension 322 and a terminal array 340 is disposed at the second end 334 of the terminal extension 322. The connector 338 defines a port 342 that is configured to receive a lead. The port 342 is open along each of two opposing ends to form a continuous passageway therethrough (i.e., the port 342 is open-ended at both ends). In at least some embodiments, the port 342 is bidirectional, whereby either end of a lead can be inserted into either end of the port 342. The port 342 extends along the connector 338 and does not extend to the second end 334 of the body 325. In at least some embodiments, the body 325 of the terminal extension 322 defines one or more lumens (not shown) that extend along a length of the terminal extension 322. These optional lumens are separate and distinct from the port 342.

A plurality of connector contacts 344 are disposed in the port 342. The plurality of connector contacts 344 are electrically coupled to the terminal array 340 of the terminal extension 322 via one or more conductors (not shown). In at least some embodiments, the number of terminals disposed on the terminal array 340 of the terminal extension 322 is equal to the number of terminals of the terminal array of the lead receivable by the port 342 (see e.g., terminal array 312b of FIG. 3A). In at least some embodiments, the terminal array 340 of the terminal extension 322 has the same length, diameter, and pitch as the terminal array of the lead receivable by the port 342 (see e.g., terminal array 312b of FIG. 3A). In at least some embodiments, the terminal array 340 of the terminal extension 322 is configured and arranged to couple with a system connector disposed on a control module (see e.g., connector 118 of the control module 102 of FIG. 1), or a lead extension (not shown), or the like.

The body 325 of the terminal extension 322 may be either more or less flexible than the body of the lead receivable by the port 342. The amount of rigidity of the terminal extension body 325 may be determined, at least in part, by the type and thickness of material used. The dimensions, such as length and cross sectional area of the terminal extension body 325 may be similar (or equal) to those of the lead body receivable by the port 342. The length of the terminal extension body 325 may be variable, ranging for example, from 1 cm to a length that is equal to, or even longer than, the lead body 307. Optionally, the connector 338 includes one or more fasteners 212 for facilitating retention of the lead in the connector 338.

Figure 3A:
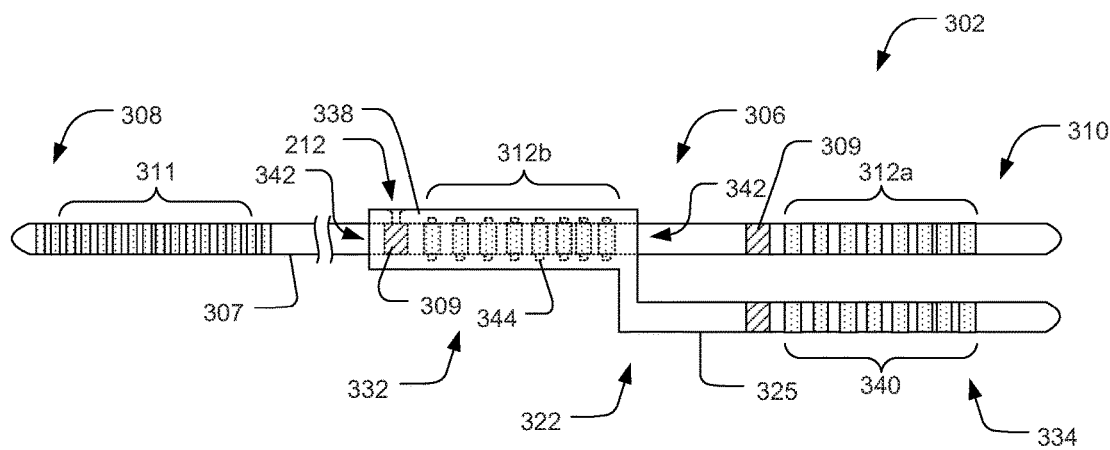
FIG. 3A is a schematic side view of one embodiment of a lead assembly having a lead with an electrode array and two terminal arrays axially-spaced-apart from one another along a length of the lead, where one of the two terminal arrays is more medially-positioned along a length of the lead than the other terminal array, and where the terminal extension of FIG. 7 is coupled to the more medially-positioned terminal array, according to the invention.

Turning to FIG. 3A, in at least some embodiments the lead receivable by the port includes multiple terminal arrays axially-spaced-apart from one another along the length of the lead. In which case, in at least some embodiments the terminal extension is configured and arranged to couple with one of the terminal arrays that is more-medially positioned than at least one other of the terminal arrays along the length of the lead. Thus, in at least some embodiments where multiple terminal arrays are disposed along the proximal end of the lead, the terminal extension is configured and arranged to couple with one of the terminal arrays that is more-distally positioned along the length of the lead than at least one other of the terminal arrays.

FIG. 3A is a schematic side view of one embodiment of a lead assembly 302 that includes a lead 306 and the terminal extension 322 coupled to the lead 306. The lead 306 includes a lead body 307 having a distal end 308 and a proximal end 310. An electrode array 311 is disposed along the distal end 308 of the lead body 307. A plurality of terminal arrays 312a and 312b are disposed along the proximal end 310 of the lead body 307. In at least some embodiments, the electrode array 311 and the terminal arrays 312a and 312b are axially-spaced-apart from one another along a length of the lead body 307.

The terminal arrays 312a and 312b are arranged along the lead body 307 with the terminal array 312a being the proximal-most of the terminal arrays 312a and 312b, and the terminal array 312b being the more medially-positioned of the terminal arrays 312a and 312b along the length of the lead body 307. In other words, the terminal array 312b is disposed distal to the proximal-most terminal array 312a.

The center-to-center spacing between adjacent terminals of the terminal arrays 312a and 312b can be any suitable distance. In at least some embodiments, the center-to-center spacing between adjacent terminals of the terminal array 312a are each equal in distance to one another. In at least some embodiments, the center-to-center spacing between adjacent terminals of the terminal array 312b are each equal in distance to one another. In at least some embodiments, the center-to-center spacing between adjacent terminals of the terminal array 312a are each equal in distance to the center-to-center spacing between adjacent terminals of the terminal array 312b.

The distance between the terminal arrays 312a and 312b can be any suitable distance. In at least some embodiments, the distance between a center of a distal-most terminal of the terminal array 312a and a center of a proximal-most terminal of the terminal array 312b is at least two times, three times, four times, five times, six times, seven times, eight times, nine times, ten times, or more the center-to-center spacing between adjacent terminals of the terminal arrays 312a and 312b.

The terminal arrays 312a and 312b may each include any suitable number of terminals. In at least some embodiments, the number of terminals in the terminal array 312a is equal to the number of terminals in the terminal array 312b. In at least some embodiments, the number of electrodes in the electrode array 311 is equal to the combined number of terminals in the terminal arrays 312a and 312b. For example, in FIG. 3A the electrode array 311 is a 16-contact array, while the terminal arrays 312a and 312b are each 8-contact arrays. In at least some embodiments, such an arrangement enables some of the electrodes of the electrode array 311 to be electrically coupled to terminals of the terminal array 312a, while other of the electrodes of the electrode array 311 are electrically coupled to terminals of the terminal array 312b.

Optionally, the connector 338 includes one or more fasteners 212 for facilitating retention of the lead 306 in the connector 338. In at least some embodiments, one or more reinforced surface regions 309 are disposed along the lead body 307 for facilitating retention of the lead 306 within the connector 338 by mating the one or more reinforced surface regions 309 with the one or more fasteners 212 of the connector 338.

The terminal extension 322 can be configured to couple with either the terminal array 312a or 312b. In at least some embodiments, the port 342 of the terminal extension 322 is configured and arranged to slidably receive the lead body 307 such that the connector contacts 344 of the connector 338 couple to the terminals of one of the terminal array 312a or 312b. In FIG. 3A, the terminal extension 322 is shown coupled to the terminal array 312b.

In FIG. 3A, eight connector contacts 344 are shown disposed in the port 342 of the terminal extension 322. It will be understood that any suitable number of connector contacts 344 may be disposed on the terminal extension 322. In at least some embodiments, the number of connector contacts 344 disposed on the terminal extension 322 is equal to the number of terminals in the terminal array to which the connector 338 is coupled. For example, in FIG. 3A the terminal array 312a includes eight terminals and the terminal extension 322 includes eight connector contacts.

When the lead includes two or more terminal arrays, it may be advantageous to couple the terminal extension 322 to one of the more-medially-located of the terminal arrays, and not couple the terminal extension 322 to the proximal-most terminal array. For example, in FIG. 3A, the terminal extension 322 is coupled to the more-medially-located terminal array 312b and is not coupled to the proximal-most terminal array 312a.

When, as shown in FIG. 3A, the terminal extension 322 is coupled to the more-medially-located terminal array 312b, the proximal-most terminal array 312a is configured and arranged to couple directly to a system connector of a control module (e.g., connector 118 of the control module 102), or a lead extension (not shown), or the like. Meanwhile, the terminal array 340 of the terminal extension 322 is configured and arranged to couple the more-medially-located terminal array 312b to another port of the system connector of a control module (e.g., connector 118 of the control module 102), or a lead extension (not shown), or another control module, or the like.

Optionally, the lead 306 may include one or more alignment features to ensure proper electrical connection between the connector contacts 344 of the terminal extension and the terminals of the terminal array 312b. Optionally, the lead 306 may include one or more alignment markers (not shown) to assist a medical practitioner in insuring proper alignment between the terminals of the lead 306 and the connector contacts 344. Alignment markers generally represent a reference point for aligning contacts of the lead 306 and the connector contacts 344. The alignment markers may be mechanical markers, radio-opaque markers, or any other type of marker known in the art.

In FIG. 3A (and in other figures), the lead is shown as being isodiametric, where the distal end and the proximal end of the lead have the same diameter. In at least some other embodiments, the distal end of the lead has a diameter that is no greater than a diameter of the proximal end of the lead. In at least some other embodiments, the distal end of the lead has a diameter that is smaller than the diameter of the proximal end of the lead.

Figure 3B:
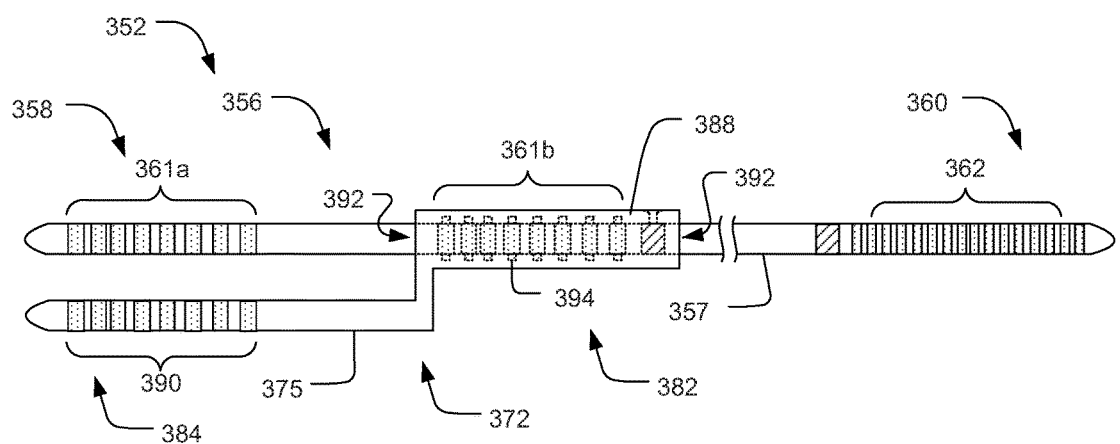
FIG. 3B is a schematic side view of one embodiment of a lead assembly having a lead with two electrode arrays and a terminal array axially-spaced-apart from one another along a length of the lead, where one of the two electrode arrays is more medially-positioned along a length of the lead than the other electrode array, and where an electrode extension is coupled to the more medially-positioned of the two electrode arrays, according to the invention.

Turning to FIG. 3B, in some embodiments the lead assembly includes a lead with a plurality of electrode arrays and an electrode extension coupleable to one or more of the plurality of electrode arrays. FIG. 3B is a schematic side view of another embodiment of a lead assembly 352 that includes a lead 356 and an electrode extension 372 coupleable to the lead 356. The lead 356 includes a lead body 357 having a distal end 358 and a proximal end 360. A plurality of electrode arrays 361a and 361b are disposed along the distal end 358 of the lead body 357. A terminal array 362 is disposed along the proximal end 360 of the lead body 357. In at least some embodiments, the electrode arrays 361a and 361b and the terminal array 362 are axially-spaced-apart from one another along a length of the lead body 357.

In FIG. 3B, the electrode arrays 361a and 361b are arranged along the lead body 357 with the electrode array 361a being the distal-most of the electrode arrays 361a and 361b, and the electrode array 361b being the more medially-positioned of the electrode arrays 361a and 361b along the length of the lead body 357.

The center-to-center spacing between adjacent electrodes of the electrode arrays 361a and 361b can be any suitable distance. In at least some embodiments, the center-to-center spacing between adjacent electrodes of the electrode array 361a are each equal in distance to one another. In at least some embodiments, the center-to-center spacing between adjacent electrodes of the electrode array 361b are each equal in distance to one another. In at least some embodiments, the center-to-center spacing between adjacent electrodes of the electrode array 361a are each equal in distance to the center-to-center spacing between adjacent electrodes of the electrode array 361b.

The distance between the electrode arrays 361a and 361b can be any suitable distance. In at least some embodiments, the distance between a center of a proximal-most electrode of the electrode array 361a and a center of a distal-most electrode of the electrode array 361b is at least two times, three times, four times, five times, six times, seven times, eight times, nine times, ten times, or more the center-to-center spacing between adjacent electrodes of the electrode arrays 361a and 361b.

The electrode extension 372 includes a body 375 having a first end 382 and an opposing second end 384. A connector 388 is disposed at the first end 382 of the electrode extension 372 and an electrode array 390 is disposed at the second end 384 of the electrode extension 372. The connector 388 defines a port 392 that is configured to receive the lead body 357. The port 392 is open along each of two opposing ends to form a continuous passageway therethrough (i.e., the port 392 is open-ended at both ends). In at least some embodiments, the port 392 is bidirectional, whereby the lead body 357 can be inserted into either end of the port 392. A plurality of connector contacts 394 are disposed in the port 392. The plurality of connector contacts 394 are electrically coupled to the terminal array 390 of the electrode extension 372 via one or more conductors (not shown).

The port 392 extends along the connector 388 and does not extend to the second end 384 of the body 375. In at least some embodiments, the body 375 of the terminal extension 372 defines one or more lumens (not shown) that extend along a length of the terminal extension 372. These optional lumens are separate and distinct from the port 392.

The electrode extension 372 can be configured to couple with either the electrode array 361a or 361b. In at least some embodiments, the port 392 of the electrode extension 372 is configured and arranged to slidably receive the lead body 357 such that the connector contacts 394 of the connector 388 can be coupled to the electrodes of one of the electrode array 361a or 361b. In FIG. 3B, the electrode extension 372 is shown coupled to the electrode array 361b.

When the lead is a percutaneous lead that includes two or more electrode arrays, it may be advantageous to couple the electrode extension 372 to one of the more-medially-located of the electrode arrays, and not couple the electrode extension 372 to the distal-most electrode array. For example, in FIG. 3B, the electrode extension 372 is shown coupled to the more-medially-located electrode array 361b and not coupled to the distal-most electrode array 361a.

When, as shown in FIG. 3B, the electrode extension 372 is coupled to the more-medially-located electrode array 361b, the electrode arrays 361a and 361b can be arranged to operate as a two-column paddle lead (see e.g., FIG. 1A). In at least some embodiments, the electrode extension 372 can be used to effectively extend the electrode array 361b to the electrode array 390. In which case, the electrode array 390 can be positioned, as desired. Thus, in at least some embodiments the electrode array 390 can be disposed side-by-side with the electrode array 361a. In which case, the two in-line electrode arrays 361a and 361b can be effectively transformed into a two-column paddle lead, where the electrode array 361a forms one of the two columns and the electrode array 390 of the electrode extension 372 forms the other of the two columns. Furthermore, in embodiments of the lead assembly that include additional electrode arrays disposed along the lead, one or more of those additional electrode arrays can be coupled to additional electrode extensions and used to form additional columns of electrodes in a side-by-side configuration, along with the electrode arrays 361a and 390.

The lead may include any suitable number of electrode arrays or terminal arrays or both axially-spaced apart from one another along the length of the lead. In FIGS. 1-2A, the lead 106 is shown having a single electrode array and a single terminal array. In FIG. 3A, the lead 306 is shown having a single electrode array and two terminal arrays. In FIG. 3B, the lead 356 is shown having two electrode arrays and a single terminal array. In at least some embodiments, three or more electrode arrays are disposed along the length of the lead. In at least some embodiments, three or more terminal arrays are disposed along the length of the lead. The lead can be configured such that the lead includes more terminal arrays than electrode arrays, fewer terminal arrays than electrode arrays, or an equal number of terminal arrays and electrode arrays. In at least some embodiments, the lead includes an equal number of terminals and electrodes, regardless of the relative number of terminal arrays or electrode arrays.

Figure 4:
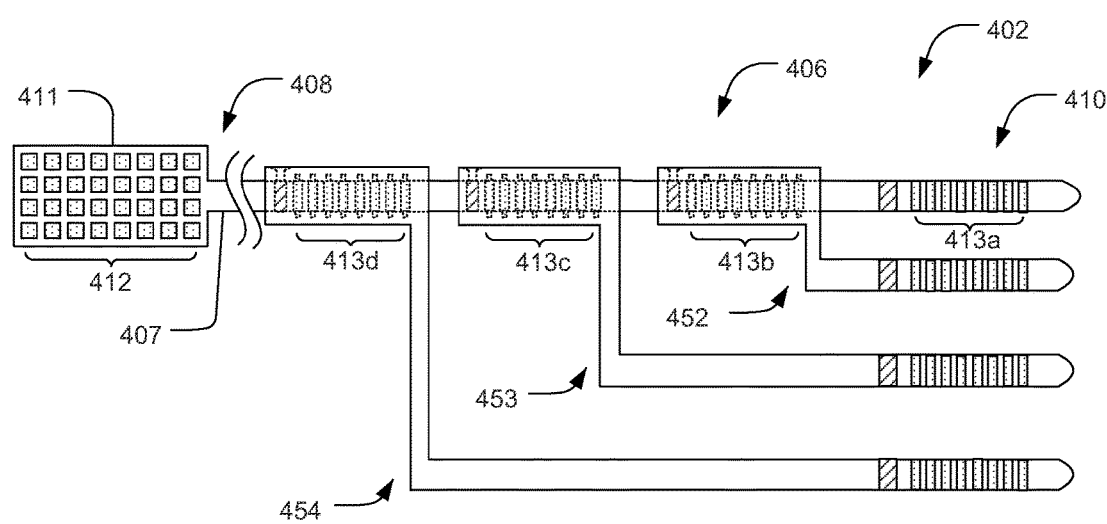
FIG. 4 is a schematic side view of another embodiment of a lead assembly, the lead assembly having a lead with an electrode array and four terminal arrays axially-spaced-apart from one another along a length of the lead, where three terminal extensions are coupled to the three most medially-positioned of the four terminal arrays, according to the invention.

Turning to FIG. 4, in at least some embodiments the lead assembly includes a plurality of electrode/terminal extensions. The lead assembly may include any suitable number of electrode/terminal extensions coupleable to any suitable number of electrode/terminal arrays. In at least some embodiments, the number of electrode/terminal extensions may be equal to two less than the total number of electrode arrays and terminal arrays disposed on the lead.

FIG. 4 is a schematic side view of one embodiment of a lead assembly 402 that includes a lead 406 and terminal extensions 452-454 coupled to the lead 406. The lead 406 includes a lead body 407 having a distal end 408 and a proximal end 410, and a paddle body 411 disposed at the distal end 408 of the lead body 407.

The lead 406 includes an electrode array 412 disposed on the paddle body 411 and a plurality of terminal arrays 413a-d axially-spaced-apart from one another along the length of the lead body 407. The terminal arrays 413a-d are arranged along the lead body 407 with the terminal array 413a being the proximal-most of the terminal arrays 413a-d along the length of the lead body 407, the terminal array 413d being the distal-most of the terminal arrays 413a-d, and the terminal arrays 413b and 413c being disposed between the terminal arrays 413a and 413d.

The terminal extensions 452-454 are coupled to the lead body 407 such that the terminal extension 452 couples to the terminal array 413b, the terminal extension 453 couples to the terminal array 413c, and the terminal extension 454 couples to the terminal array 413d, while the contact array 413a is configured for direct connection with a control module (or a lead extension). In at least some embodiments, the number of electrodes in the electrode array 412 is equal to the combined number of terminals in the terminal arrays 413a-d. For example, in FIG. 4 the electrode array 412 is a 32-electrode array, while the terminal arrays 413a-d are each 8-contact arrays.

Figure 5:
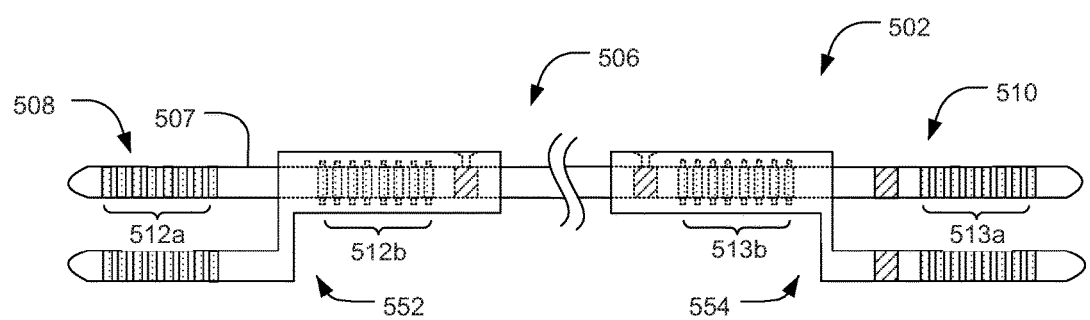
FIG. 5 is a schematic side view of yet another embodiment of a lead assembly, the lead assembly having a lead with two electrode arrays and two terminal arrays axially-spaced-apart from one another along a length of the lead, where an electrode extension is coupled to the more-medially positioned of the two electrode arrays and a terminal extension is coupled to the more-medially positioned of the two terminal arrays, according to the invention.

Turning to FIG. 5, in at least some embodiments the lead assembly includes both at least one electrode extension coupled to an electrode array of the lead and at least one terminal extension coupled to a terminal array of the lead. FIG. 5 is a schematic side view of one embodiment of a lead assembly 502 that includes a lead 506, an electrode extension 552, and a terminal extension 554, where the electrode extension 552 and the terminal extension 554 are coupled to the lead 506. The lead 506 includes a lead body 507 having a distal end 508 and a proximal end 510.

The lead 506 includes a plurality of electrode arrays 512a and 512b and a plurality of terminal arrays 513a and 513b all axially-spaced-apart from one another along the length of the lead body 507. The electrode arrays 512a and 512b are arranged along the lead body 507 with the electrode array 512a being the distal-most of the electrode arrays 512a and 512b, while the electrode array 512b is the more-medially positioned of the electrode arrays 512a and 512b along the length of the lead body 507. The terminal arrays 513a and 513b are each disposed proximal to both of the electrode arrays 512a and 512b along the length of the lead body 507. The terminal arrays 513a and 513b are arranged along the lead body 507 with the terminal array 513a being the proximal-most of the terminal arrays 513a and 513b, while the terminal array 513b is the more-medially positioned of the terminal arrays 513a and 513b along the length of the lead body 507.

The electrode extension 552 is coupled to the lead 506 such that the electrode extension 552 couples to the electrode array 512b. The terminal extension 554 is coupled to the lead 506 such that the terminal extension 554 couples to the terminal array 515b. In other words, the electrode extension 552 is coupled to the more-medially positioned of the electrode arrays, and the terminal extension 554 is coupled to the more-medially positioned of the terminal arrays.

Figure 6:
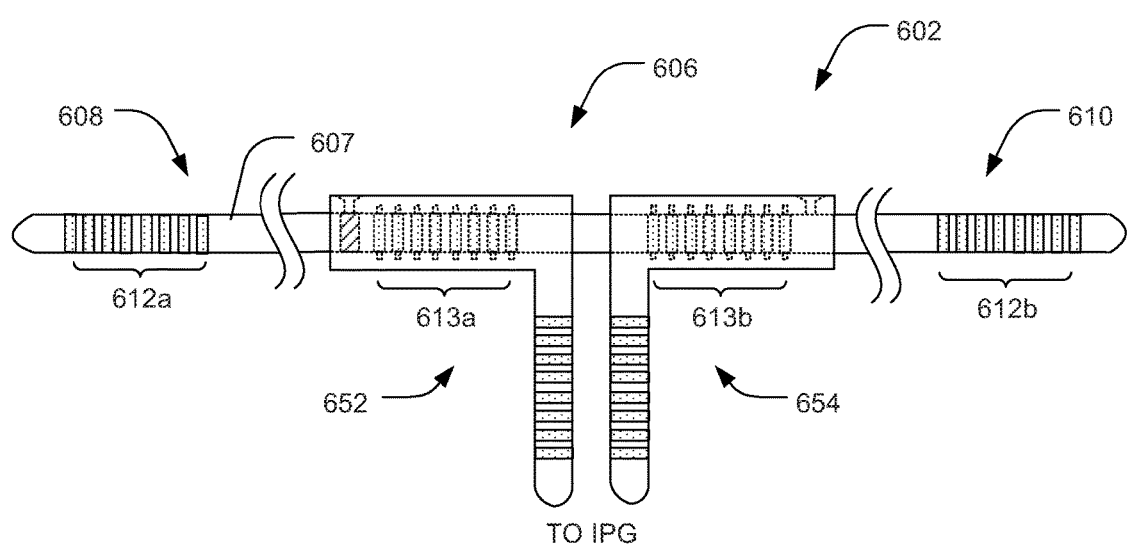
FIG. 6 is a schematic side view of another embodiment of a lead assembly, the lead assembly having a lead with two electrode arrays and two terminal arrays axially-spaced-apart from one another along a length of the lead, where the two terminal arrays are each positioned medial to the two electrode arrays along the length of the lead, and where each of two terminal extensions is coupled to a different one of the terminal arrays, according to the invention.

Turning to FIG. 6, the one or more terminal arrays and the one or more electrode arrays can be axially-spaced apart from one another along the length of the lead in any suitable relative arrangement. In at least some embodiments, at least one electrode array is disposed proximal to at least one terminal array. In at least some embodiments, one or more electrode arrays are disposed at the distal end of the lead, one or more electrode arrays are disposed at the proximal end of the lead, and one or more terminal arrays are intermediately-positioned between the one or more electrode arrays disposed at the distal end of the lead and the one or more electrode arrays disposed at the proximal end of the lead.

FIG. 6 is a schematic side view of one embodiment of a lead assembly 602 that includes a lead 606 and terminal extensions 652 and 654 coupled to the lead 606. The lead 606 includes a lead body 607 having a distal end 608 and a proximal end 610.

The lead 606 includes a plurality of electrode arrays 612a and 612b and a plurality of terminal arrays 613a and 613b all axially-spaced-apart from one another along the length of the lead body 607. The electrode arrays 612a and 612b are axially-spaced-apart from one another along the lead body 507 with the electrode array 612a being disposed along the distal end 608 of the lead body 607, while the electrode array 612b is dispose along the proximal end 610 of the lead body 607. The terminal arrays 613a and 613b are each disposed proximal to the electrode array 612a and distal to the electrode array 612b along the length of the lead body 607.

The terminal extensions 652 and 654 are coupled to the lead 606 such that the terminal extension 652 couples to the terminal array 613a, and the terminal extension 654 couples to the terminal array 613b. Consequently, the terminal extensions 652 and 654 are both coupled to terminal arrays 613a and 613b which are intermediately-positioned along the length of the lead 606, while the electrode arrays 612a and 612b are disposed along each end of the lead 606. Such a configuration may be useful for concurrent placement of electrode arrays at two different body locations that are separated from one another by up to nearly an entire length of the lead 606 and that would not otherwise be available for concurrent stimulation without using an additional lead.

Arranging two or more terminals arrays axially along the lead enables the entire length of the lead to be isodiametric. Providing an isodiametric lead may enable the lead to be introduced into the patient in a smaller needle than would otherwise be possible for a lead having multiple proximal ends, where each of the different proximal ends includes a different terminal array. Moreover, such an arrangement facilitates manufacturing of leads as compared to leads having a single terminal array because, due to tight pitches between adjacent terminals of a given terminal array, it is easier to form multiple terminal arrays of fewer terminals each with tight pitches than forming a single array with additional terminals at the same pitch.

When the lead assembly includes three or more electrode/terminal arrays disposed on the lead, the portions of the lead body between adjacent arrays (or between an electrode/terminal array and one of the ends of the lead) may, in at least some embodiments, be of equal rigidity. In other embodiments, at least one lead body portion between two adjacent electrode/terminal arrays (or between an electrode/terminal array and one of the tips of the lead) may have a rigidity that is different from at least one other lead body portion between two adjacent electrode/terminal arrays (or between an electrode/terminal array and one of the tips of the lead).

For example, in at least some embodiments where the lead includes three or more electrode/terminal arrays, the portion of the lead body between the proximal-most electrode/terminal array and the nearest intermediately-positioned electrode/terminal array is more rigid than at least one other lead body portion between two adjacent electrode/terminal arrays (or between an electrode/terminal array and one of the tips of the lead). It may be an advantage to form the lead body in such an arrangement to provide enough rigidity at the proximal end of the lead to facilitate insertion of the proximal end of the lead into the connector, while enabling the remaining portions of the lead body to be more flexible to facilitate navigation through tortuous blood vessels.

It will be understood that the above-described terminal extensions and electrode extensions may, in at least some embodiments, have the same components. In at least some embodiments, the electrode extension and the terminal extension are distinguished only by whether the connector of the electrode/terminal extension is coupled to an electrode array or a terminal array. In at least some other embodiments, the body of the electrode array may vary from the body of the terminal array by one or more mechanical properties including, for example, materials, length, width, shape, or the like.

It will be understood that the above-described exemplary arrangements with 8, 16, and 32 electrode/terminal arrays are not meant to be limiting and are merely used for illustration. The lead assembly may include leads having any suitable number of electrode/terminal arrays. It will also be understood that, in the case of lead assemblies with terminal extensions, the terminal extensions may be coupleable to lead extension terminal arrays in addition to, or in lieu of, one or more lead terminal arrays.

Embodiments of the present disclosure may be used in any medical or non-medical procedure, including any medical procedure where one or more body part requires electrical stimulation. In addition, at least certain aspects of the aforementioned embodiments may be combined with other aspects of the embodiments, or removed, without departing from the scope of the preset disclosure.

While the present disclosure has been described by means of specific embodiments and applications thereof, numerous modifications and variations could be made thereto by those skilled in the art without departing from the scope of the present disclosure set forth in the claims.

What is claimed as new and desired to be protected under United States Letters Patent is:

1. A lead assembly for an implantable electrical stimulation system comprising:
   a lead configured and arranged for insertion into a patient, the lead comprising
   a lead body having a distal end, a proximal end, and a longitudinal length,
   a plurality of electrodes disposed along the distal end of the lead body, the plurality of electrodes arranged into a plurality of electrode arrays, each electrode array comprising a plurality of the electrodes, wherein the plurality of electrode arrays comprises a distal-most electrode array and a medial electrode array axially-spaced-apart from one another along the longitudinal length of the lead body with the medial electrode array being disposed proximal to the distal-most electrode array along the longitudinal length of the lead body, and a plurality of terminals disposed along the proximal end of the lead body, the plurality of terminals arranged into at least one terminal array, a plurality of conductors electrically coupling the plurality of electrodes to the plurality of terminals; and an electrode extension configured and arranged to electrically couple to the medial electrode array, the electrode extension comprising an electrode extension body having a first end and an opposing second end, an electrode extension connector disposed at the first end of the electrode extension body, a port defined in the electrode extension connector, the port having a first open end and an opposing second open end and forming a continuous passageway therebetween, the port configured and arranged to receive the medial electrode array and to permit the lead body to extend through both of the first open end and the opposing second open end when the medial electrode array is received by the port, a connector contact array comprising a plurality of connector contacts disposed within the port, the connector contact array configured and arranged to couple electrically with electrodes of the medial electrode array when the medial electrode array is received by the port, an electrode extension electrode array comprising a plurality of electrodes disposed along the second end of the electrode extension body, and a plurality of electrode extension conductors electrically coupling the connector contact array to the electrode extension electrode array.

2. The lead assembly of claim 1, wherein the at least one terminal array is configured and arranged for insertion into a system connector of one of a control module or a lead extension.

3. The lead assembly of claim 1, wherein the medial electrode array is a first medial electrode array, and wherein the plurality of electrode arrays further comprises a second medial electrode array axially-spaced-apart from the first medial electrode array and the distal-most electrode array along the longitudinal length of the lead body with the second medial electrode array being disposed proximal to the distal-most electrode array along the longitudinal length of the lead body.

4. The lead assembly of claim 3, wherein the electrode extension is a first electrode extension, and wherein the lead assembly further comprises a second electrode extension configured and arranged to electrically couple to the second medial electrode array.

5. The lead assembly of claim 1, wherein the distal end of the lead body has a diameter that is smaller than a diameter of the proximal end of the lead body.

6. The lead assembly of claim 1, wherein the lead body is more rigid between the distal-most electrode array and the medial electrode array than between the medial electrode array and the at least one terminal array.

7. The lead assembly of claim 1, wherein the lead body is isodiametric.

8. The lead assembly of claim 1, wherein the lead is a paddle lead.

9. The lead assembly of claim 1, wherein a center-to-center spacing between adjacent electrodes of the distal-most electrode array and a center-to-center spacing between adjacent electrodes of the medial electrode array are each equal in distance to one another.

10. The lead assembly of claim 9, wherein a distance between a center of a proximal-most electrode of the distal-most electrode array and a center of a distal-most electrode of the medial electrode array is at least two times larger than the center-to-center spacing between adjacent electrodes of the distal-most electrode array and the medial electrode array.

11. An electrical stimulation system comprising:
the lead assembly of claim 1;
a control module configured and arranged to electrically couple to the lead assembly, the control module comprising
a housing, and
an electronic subassembly disposed in the housing; and
at least one system connector configured and arranged for receiving a portion of the lead body, the at least one system connector having a proximal end, a distal end, and a longitudinal length, the at least one system connector comprising
a connector housing defining a port at the distal end of the at least one system connector, the port configured and arranged for receiving the proximal end of the lead body, and
a plurality of connector contacts disposed in the connector housing, the plurality of connector contacts configured and arranged to couple to one of the at least one terminal array of the lead.

12. The electrical stimulation system of claim 11, wherein a one of the at least one system connector is disposed on the control module.

13. The electrical stimulation system of claim 11, further comprising a lead extension configured and arranged to couple the lead to the control module, wherein a one of the at least one system connector is disposed on the lead extension.

14. The electrical stimulation system of claim 11, wherein the at least one terminal array is a plurality of terminal arrays, wherein the plurality of terminal arrays comprises a proximal-most terminal array and a medial terminal array axially-spaced-apart from one another along the longitudinal length of the lead body with the medial terminal array being disposed distal to the proximal-most terminal array along the longitudinal length of the lead body.

15. The electrical stimulation system of claim 14, further comprising:
a terminal extension configured and arranged to electrically couple to the medial terminal array, the terminal extension comprising
a terminal extension body having a first end and an opposing second end,
a terminal extension connector disposed at the first end of the terminal extension body,
a port defined in the terminal extension connector, the port having a first open end and an opposing second open end and forming a continuous passageway therebetween, the port configured and arranged to receive the medial terminal array and to permit the lead body to extend through both of the first open end and the opposing second open end when the medial terminal array is received by the port, a connector contact array comprising a plurality of connector contacts disposed within the port, the connector contact array configured and arranged to couple electrically with terminals of the medial terminal array when the medial terminal array is received by the port, a terminal extension terminal array comprising a plurality of terminals disposed along the second end of the terminal extension body, and a plurality of terminal extension conductors electrically coupling the connector contact array to the terminal extension terminal array.

16. The electrical stimulation system of claim 14, wherein the lead body is isodiametric.

17. The electrical stimulation system of claim 11, wherein the at least one terminal array is a plurality of terminal arrays, wherein the plurality of terminal arrays comprises a first medial terminal array and a second medial terminal array axially-spaced-apart from one another along the longitudinal length of the lead body, and wherein the first medial terminal array and the second medial terminal array are both distal to the medial electrode array and proximal to the distal-most electrode array along the longitudinal length of the lead body.

18. The electrical stimulation system of claim 17, further comprising:

a first terminal extension configured and arranged to electrically couple to the first medial terminal array, the first terminal extension comprising a first terminal extension body having a first end and an opposing second end, a connector disposed at the first end of the first terminal extension body, a port defined in the connector, the port having a first end and an opposing second end and forming a continuous passageway therebetween, the port configured and arranged to receive the first medial terminal array, a connector contact array comprising a plurality of connector contacts disposed within the port, the connector contact array configured and arranged to couple electrically with terminals of the first medial terminal array when the first medial terminal array is received by the port, a first terminal extension terminal array comprising a plurality of terminals disposed along the second end of the first terminal extension body, and a plurality of first terminal extension conductors electrically coupling the connector contact array to the first terminal extension terminal array.

19. The electrical stimulation system of claim 18, further comprising:

a second terminal extension configured and arranged to electrically couple to the second medial terminal array, the second terminal extension comprising a second terminal extension body having a first end and an opposing second end, a connector disposed at the first end of the second terminal extension body, a port defined in the connector, the port having a first end and an opposing second end and forming a continuous passageway therebetween, the port configured and arranged to receive the second medial terminal array, a connector contact array comprising a plurality of connector contacts disposed within the port, the connector contact array configured and arranged to couple electrically with terminals of the second medial terminal array when the second medial terminal array is received by the port, a second terminal extension terminal array comprising a plurality of terminals disposed along the second end of the terminal extension body, and a plurality of terminal extension conductors electrically coupling the connector contact array to the second terminal extension terminal array.

20. The electrical stimulation system of claim 17, wherein the lead body is isodiametric.

* * * * *